US011865301B2

(12) United States Patent
Leard et al.

(10) Patent No.: US 11,865,301 B2
(45) Date of Patent: Jan. 9, 2024

(54) PROTECTIVE COVER FOR MEDICAL SPIKE PRODUCTS

(71) Applicant: Avent, Inc., Alpharetta, GA (US)

(72) Inventors: Brett C. Leard, Seneca, SC (US); Ruoya Wang, Decatur, GA (US); Gavin H. Mannion, Atlanta, GA (US); Khoa T. Lien, Alpharetta, GA (US); Collin Widger, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 132 days.

(21) Appl. No.: 17/137,836

(22) Filed: Dec. 30, 2020

(65) Prior Publication Data
US 2022/0203024 A1 Jun. 30, 2022

(51) Int. Cl.
*A61M 5/162* (2006.01)
*B65D 73/00* (2006.01)

(52) U.S. Cl.
CPC ....... *A61M 5/1626* (2013.01); *B65D 73/0085* (2013.01); *A61M 2205/02* (2013.01)

(58) Field of Classification Search
CPC ................ A61M 5/002; A61M 5/1626; A61M 2205/02; A61B 17/06161; A61B 2090/0801; B65D 73/0085
USPC ...... 206/485, 63.3, 349, 363, 438, 476, 486, 206/482, 446, 463, 380, 382, 780, 327, 206/347, 364–365, 464, 571, 763; 220/6; 229/84, 87.01, 103.3; 53/397
See application file for complete search history.

(56) References Cited

U.S. PATENT DOCUMENTS

| 2,229,427 | A | * | 1/1941 | Tanner | A47F 5/112 206/45.3 |
| 3,339,608 | A | * | 9/1967 | Brenner | B26B 29/00 206/349 |
| 3,411,620 | A | * | 11/1968 | Steinbock | A61M 25/002 206/364 |
| 4,014,434 | A | * | 3/1977 | Thyen | A61F 6/14 206/476 |

(Continued)

FOREIGN PATENT DOCUMENTS

EP 3100697 A1 12/2016

OTHER PUBLICATIONS

International Search Report and Written Opinion received in PCT/US2021/065614 dated Apr. 7, 2022, 13 pages.

*Primary Examiner* — Chun Hoi Cheung
*Assistant Examiner* — Brijesh V. Patel
(74) *Attorney, Agent, or Firm* — Meunier Carlin & Curfman LLC

(57) ABSTRACT

A protective cover or sleeve for a medical spike product is provided. The protective cover includes a first panel having a lower edge, and a second panel having a lower edge, wherein the first panel and the second panel are connected at their lower edges, respectively. The first panel and the second panel are configured to be spaced apart to form a protective sleeve. The protective sleeve is configured to receive the medical spike product such that the first panel and the second panel protectively cover and enable aseptic handling of a spike end of the medical spike product and prevent the spike end from breaching a sterile barrier. The protective sleeve may be made from a paper-based material. A medical spike product assembly including the protective cover and a medical spike product inserted therein is also provided.

20 Claims, 4 Drawing Sheets

(56) References Cited

U.S. PATENT DOCUMENTS

| | | | | |
|---|---|---|---|---|
| 4,023,678 | A * | 5/1977 | Fiedler | A61F 6/14 206/476 |
| 4,046,251 | A * | 9/1977 | Bruml | B65D 5/5023 206/463 |
| 4,111,302 | A * | 9/1978 | Roth | A61F 6/14 206/363 |
| 4,121,711 | A * | 10/1978 | Bolanowski | A61B 17/06138 206/382 |
| 4,135,623 | A * | 1/1979 | Thyen | A61B 17/06138 206/227 |
| 4,142,632 | A * | 3/1979 | Sandel | A61B 50/20 206/478 |
| 4,171,050 | A * | 10/1979 | Murray | B65D 73/0085 206/463 |
| 4,201,294 | A * | 5/1980 | Roccaforte | B65D 75/04 248/152 |
| 4,266,664 | A * | 5/1981 | Dixon | B65D 75/02 206/349 |
| 4,506,787 | A * | 3/1985 | Bruso | A61B 50/20 206/363 |
| 4,671,408 | A * | 6/1987 | Raines | A61M 5/002 206/45.23 |
| 4,899,877 | A * | 2/1990 | Kiernan | B65D 75/245 206/349 |
| 4,921,096 | A * | 5/1990 | McFarlane | A61M 25/002 206/349 |
| 5,048,678 | A * | 9/1991 | Chambers | B65D 71/10 206/476 |
| 5,076,431 | A * | 12/1991 | Thompson | A61B 50/30 206/382 |
| 5,101,968 | A * | 4/1992 | Henderson | A61B 17/06138 206/227 |
| 5,131,542 | A * | 7/1992 | Stenstrom | B65D 71/10 206/476 |
| 5,168,997 | A * | 12/1992 | Czopor, Jr. | B65D 75/02 229/87.01 |
| 5,199,561 | A * | 4/1993 | Roshdy | A61B 17/06138 206/382 |
| 5,219,077 | A * | 6/1993 | Transue | A61F 2/0063 206/483 |
| 5,236,082 | A * | 8/1993 | Brown | A61B 17/06138 206/382 |
| 5,351,822 | A * | 10/1994 | Sinn | B65D 73/0021 206/478 |
| 5,375,717 | A * | 12/1994 | Roshdy | A61B 17/06138 206/227 |
| 5,379,894 | A * | 1/1995 | Haas | B65D 75/14 206/532 |
| 5,474,179 | A * | 12/1995 | Losif | A61F 5/451 206/521 |
| 5,577,606 | A * | 11/1996 | Schwentuchowski | B65D 73/0078 206/349 |
| 5,601,189 | A * | 2/1997 | Roshdy | A61B 17/06138 206/227 |
| 5,692,611 | A * | 12/1997 | Harrison | B65D 75/14 206/532 |
| 5,699,909 | A * | 12/1997 | Foster | B65D 77/26 206/370 |
| 5,788,063 | A * | 8/1998 | Van Ness | B65D 73/0078 206/349 |
| 5,842,567 | A * | 12/1998 | Rowe | A61B 50/3001 206/464 |
| 5,871,089 | A * | 2/1999 | Odermatt | A61B 17/06138 206/227 |
| 5,924,567 | A * | 7/1999 | Wenum | A46B 17/04 206/15.3 |
| 5,954,202 | A * | 9/1999 | Mellon | B65D 75/14 206/532 |
| 5,975,294 | A * | 11/1999 | Hsi-Chang | B65D 73/0078 206/349 |
| 6,691,868 | B2 * | 2/2004 | Roshdy | A61B 50/30 206/366 |
| 7,434,684 | B1 * | 10/2008 | Mabra | F42B 39/007 220/4.23 |
| 8,413,810 | B2 * | 4/2013 | Merboth | A61B 50/30 206/204 |
| 8,517,173 | B2 * | 8/2013 | Gui | B65D 25/28 206/349 |
| 8,517,174 | B2 * | 8/2013 | Dacey | A61F 2/0095 206/63.3 |
| 8,540,139 | B2 * | 9/2013 | Dacey | A61F 2/0095 220/6 |
| 9,701,455 | B2 * | 7/2017 | Jones | B65D 73/0078 |
| 9,776,783 | B2 * | 10/2017 | Nadig | B65D 77/04 |
| 9,999,469 | B2 * | 6/2018 | Roesler | A61B 50/30 |
| 10,336,522 | B2 * | 7/2019 | Jones | B65D 73/0078 |
| 2003/0029737 | A1 * | 2/2003 | Alpern | A61B 17/06133 206/63.3 |
| 2004/0020795 | A1 * | 2/2004 | Braginsky | A61B 17/06138 606/228 |
| 2014/0343553 | A1 | 11/2014 | Ford et al. | |
| 2018/0071043 | A1 | 3/2018 | Dacey et al. | |
| 2018/0214230 | A1 * | 8/2018 | Jacobs | A61B 90/70 |

* cited by examiner

PROTECTIVE COVER FOR MEDICAL SPIKE PRODUCTS

FIELD OF THE INVENTION

The subject matter of the present invention relates generally to a protective cover for medical spike products.

BACKGROUND

Medical spike products are implemented for a variety of uses and procedures in the healthcare industry. For example, an IV spike is typically used to access the fluid within an IV bag and provide a connection for tubing to transfer fluid from the IV bag. Often, medical spike products do not utilize any package covering. Without any packaging or covering, the medical spike products are not maintained in a sterile condition. Moreover, the medical spike products may be vulnerable to physical damage when they are not provided with any packaging or covering. Alternatively, the generally accepted method to prevent damage and maintain aseptic handling of a medical spike product is to provide a single-use cover, such as a cap or sleeve. These single-use covers are often formed from single-use polymer materials. Although such covers may prevent undesirable damage to the medical spike product, the single-use nature of the covers creates additional medical waste. As the healthcare industry continues to grow, the increasing amount of medical waste is causing a rising medical waste problem. These increases in waste due to single-use products are detrimental to the environment.

Moreover, medical spike products may be provided in conjunction with other medical apparatus having a sterile barrier. When the medical spike product is included in a package, there is a risk of the medical spike product puncturing or otherwise breaching the sterile barrier.

Consequently, there is a need for protective cover for medical spike products that can protect from physical damage and is environmentally friendly. In particular, a protective cover for medical spike products that is environmentally friendly and maintains aseptic handling and sterility in compliance with industry standards would also be useful.

SUMMARY

Objects and advantages of the invention will be set forth in part in the following description, or may be obvious from the description, or may be learned through practice of the invention.

The present invention is directed to a protective cover for a medical spike product. The protective cover includes a first panel having a lower edge; and a second panel having a lower edge. The first panel and the second panel are connected at their lower edges, respectively. The first panel and the second panel are configured to be spaced apart to form a protective sleeve, wherein the sleeve is configured to receive the medical spike product such that the first panel and the second panel protectively cover a spike end of the medical spike product.

In one particular embodiment, the first panel can include an upper edge opposite the lower edge of the first panel, a right-side edge, and a left-side edge, wherein the right-side edge can include an angled portion adjacent to the lower edge, and the left-side edge can include an angled portion adjacent to the lower edge. Further, a first right-side angle may be formed between the right-side angled portion and the lower edge, and a first left-side angle may be formed between the left-side angled portion and the lower edge. Further, the first right-side angle and the first left-side angle can be obtuse. Moreover, the first right-side angle and the first left-side angle can be equal.

Further, the second panel can include an upper edge opposite the lower edge of the second panel, a right-side edge, and a left-side edge, wherein the right-side edge can include an angled portion adjacent to the lower edge, and the left-side edge comprises an angled portion adjacent to the lower edge. Moreover, a second right-side angle can be formed between the right-side angled portion of the second panel and the lower edge of the second panel, and a second left-side angle can be formed between the left-side angled portion of the second panel and the lower edge of the second panel. Moreover, the second right-side angle can be equal to the first right-side angle, and the second left-side angle is equal to the first right-side angle.

In another embodiment, the first panel and the second panel can be bilaterally symmetrical.

In an additional embodiment, the second panel can include: a right-side edge, a right-side panel extending from the right-side edge, a left-side edge and a left-side panel extending from the left-side edge; wherein the right-side panel and the left-side panel can be configured to be secured to the top panel to form the protective opening between the first panel and the second panel. Moreover, the second panel can include a right-side fold line between the right-side edge and the right-side panel, and a left-side fold line between the left-side edge and the left-side panel; wherein the right-side panel can be folded toward the second panel along the right-side fold line and the left-side panel can be folded toward the second panel along the left-side fold line. Further, the right-side panel can be secured to the first panel and the left-side panel can be secured to the first panel. Moreover, the right-side panel and the left-side panel can be secured to the first panel with adhesive.

In yet another embodiment, the protective cover can be formed from a single piece of material. Further, the single piece of material can include a crease line along the bottom edge of the first panel and the bottom edge of the second panel; wherein the single piece of material can be folded along the crease line to bring an inner surface of the first panel adjacent to an inner surface of the second panel.

In a further embodiment, the first panel and the second panel each can include an aperture adjacent to an upper edge of the first panel and the second panel, respectively, wherein the aperture can be configured to receive a portion of the medical spike product to hold the spike end of the medical spike product within the protective sleeve.

In an additional embodiment, the protective cover can be formed from a paper-based material. Moreover, the paper-based material can be solid bleached sulfate.

In one more embodiment, the protective cover can be formed from a biodegradable material.

The present invention is further directed to a medical spike product assembly. The assembly includes a medical spike product comprising a body having a spike end. The assembly further includes a protective cover having: a first panel having a lower edge and first and second side edges; and a second panel having a lower edge and first and second side edges. The first panel and the second panel are connected at their lower edges and first and second side edges, respectively. The first panel and the second panel are configured to be spaced apart to form a protective sleeve. The spike end of the medical spike product is inserted within the protective sleeve.

In one particular embodiment, the body of the medical spike product can include opposing wings extending generally perpendicular to the spike end, further wherein the first panel and the second panel of the protective cover each comprises an aperture configured to receive the respective opposing wings of the medical spike product in order to hold the spike end of the medical spike product within the protective sleeve; wherein the opposing wings of the medical spike product are configured to be disengaged from the apertures of the first panel and the second panel, respectively, by squeezing the first and second side edges of the first panel and the second panel to separate the first panel from the second panel.

In another embodiment, the body of the medical spike product can include opposing wings extending generally perpendicular to the spike end, further wherein the first panel and the second panel of the protective cover each comprises an aperture configured to receive the respective opposing wings of the medical spike product in order to hold the spike end of the medical spike product within the protective sleeve;

wherein the opposing wings of the medical spike product are configured to be forcibly removed from the apertures of the first panel and the second panel, respectively, by tearing an upper edge of each respective aperture.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
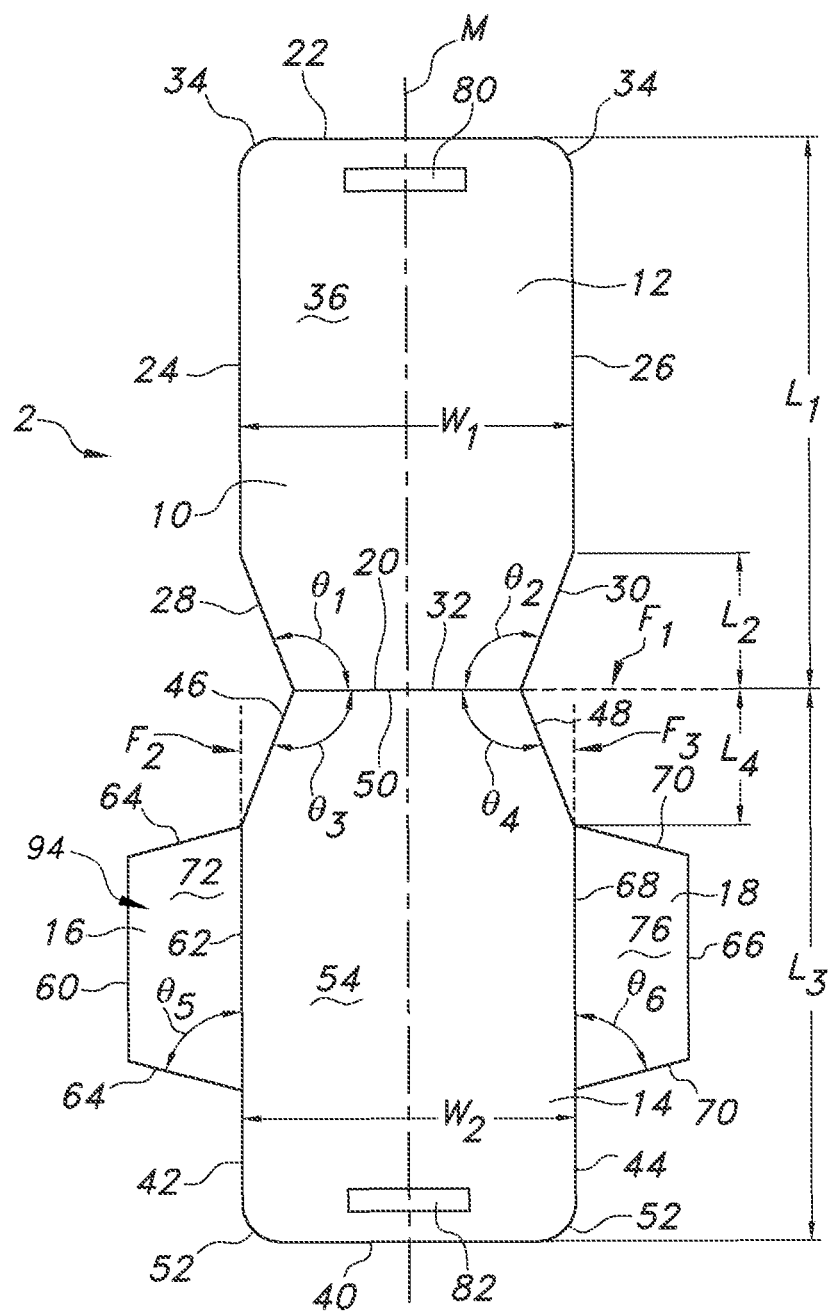
FIG. 1 illustrates a front view of a protective cover for a medical spike product prior to assembly according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a protective cover for a medical spike product. The protective cover includes a first panel having a lower edge, and a second panel having a lower edge, wherein the first panel and the second panel are connected at their lower edges, respectively. The first panel and the second panel are configured to be spaced apart to form a protective sleeve, wherein the sleeve is configured to receive the medical spike product such that the first panel and the second panel protectively cover a spike end of the medical spike product. The protective cover can be formed from a paper-based material. The present inventors have found that the paper-based protective cover for a medical spike product of the present invention achieves the goals of protecting the structure and sterility of the medical spike product while being more eco-friendly than existing single-use polymer-based alternatives. Thus, the protective cover of the present invention may prevent blunting of a medical spike product inserted therein, and prevent puncturing of the packaging or a sterile barrier that is typically recurrent by a sharp polymer-based medical spike product. As such, the protective cover of the present invention may protect any medical device products packaged with the medical spike product from a sterile barrier breach caused by the spike. The specific features of the protective cover for a medical spike product of the present invention may be better understood with reference to FIGS. 1-6.

Figure 4:
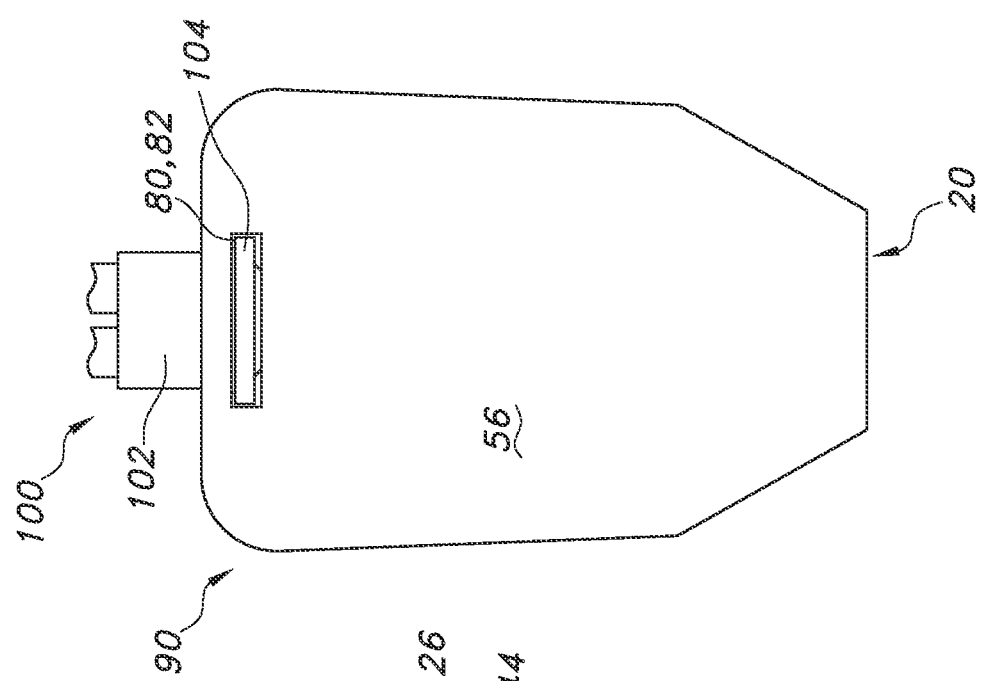
FIG. 4 illustrates a front view of a medical spike assembly having a medical spike product inserted within the protective cover of FIG. 1.

Referring now to FIG. 1, one embodiment of the protective cover 2 of the present invention is shown. The protective cover 2 is formed from a body 10 having a first panel 12 and a second panel 14. The first panel 12 and the second panel 14 are connected along a crease line 20. The second panel 14 additionally includes at least a right panel 16 and a left panel 18. When the body 10 is folded along the crease line 20, a protective sleeve 90 having a protective opening 92 is formed between the first panel 12 and the second panel 14 which can receive a spike end 106 of an IV spike 100, as shown in FIGS. 3-5 and described in more detail below.

Figure 5:
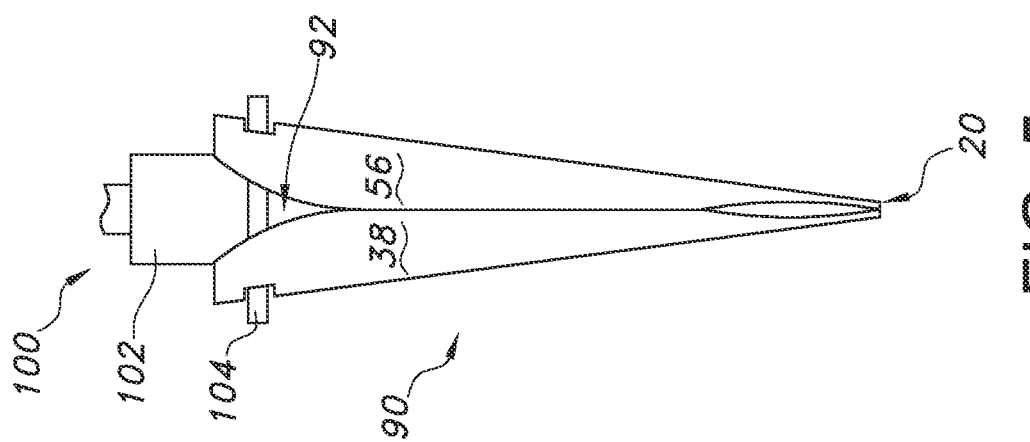
FIG. 5 illustrates a side view of the medical spike assembly of FIG. 4.
Figure 3:
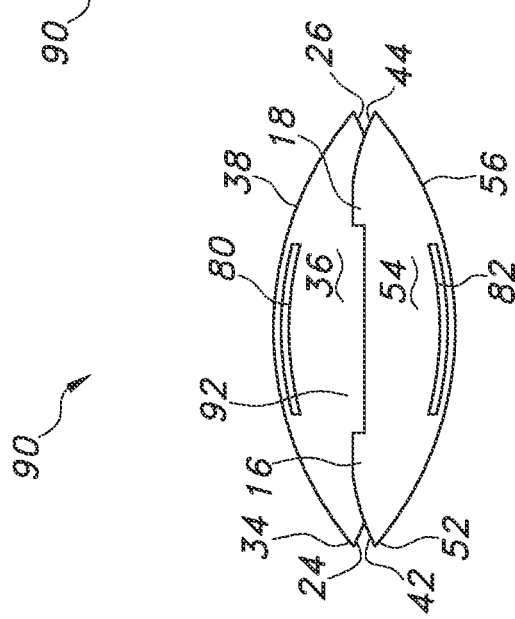
FIG. 3 illustrates a top view of the assembled protective cover of FIG. 2.
Figure 6:
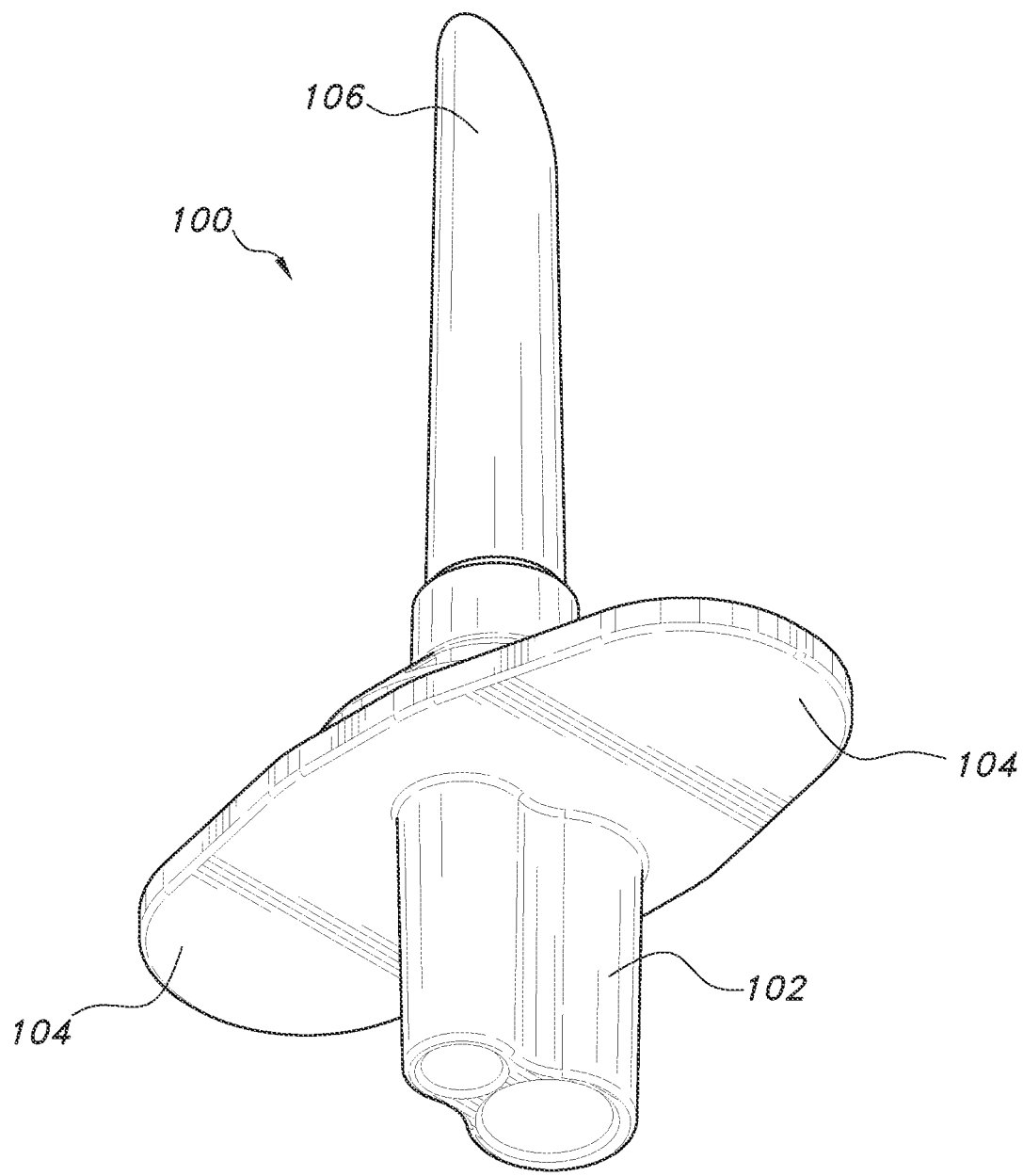
FIG. 6 illustrates a perspective view of an exemplary medical spike product that can be inserted within the protective cover of the present invention.

As shown in FIG. 1, the first panel 12, which may also be called a top panel, has an inner surface 36, and an opposite outer surface 38 (see FIGS. 3 and 5). The first panel 12 has a lower edge 32 positioned at the crease line 20. The first panel 12 additionally includes an upper edge 22 that can be opposite and generally parallel to the lower edge 32, a left-side edge 24 that can extend between the upper edge 22 and the lower edge 32, and a right-side edge 26 that can extend between the upper edge 22 and the lower edge 32 opposite the left-side edge 24. Optionally, the first panel 12 may include rounded corners 34 disposed at the transition between the left-side edge 24 and the upper edge 22, and the right-side edge 26 and the upper edge 22, respectively. The left-side edge 24 and the right-side edge 26 may each extend downward from the upper edge 22 at a perpendicular angle.

The left-side edge 24 can include an angled portion 28 disposed adjacent to the lower edge 32 with an angle θ1 between the angled portion 28 and the lower edge 32. The angle θ1 may be an obtuse angle greater than 90 degrees and less than 180 degrees, such as an angle in a range from about 100 degrees to about 160 degrees, such as from about 110 degrees to about 135 degrees. Additionally, the angled portion 28 may instead have a radiused or curved transition between the left-side edge 24 and/or the lower edge 32. Similarly, the right-side edge 26 can include an angled portion 30 disposed adjacent to the lower edge 32 with an angle θ2 between the angled portion 28 and the lower edge 32. The angle θ2 may be an obtuse angle greater than 90 degrees and less than 180 degrees, such as an angle in a range from about 100 degrees to about 160 degrees, such as from about 110 degrees to about 135 degrees. Additionally, the angled portion 30 may instead have a radiused or curved transition between the right-side edge 26 and/or the lower edge 32. In some aspects of the invention, the angles θ1 and θ2 can be equal, and/or a radius of curvature of the angled portions 28 and 30 can be equal. Moreover, in some aspects of the invention, the first panel 12 may be bilaterally symmetrical across a midline M of the body 10 such that the left-side edge 24, the angled portion 28 of the left-side edge 24, and the angle θ1 are mirrored by the right-side edge 26, the angled portion 30 of the right-side edge 30, and the angle θ2.

As shown in FIG. 1, the first panel 12 can have a length L1 extending from the upper edge 22 to the lower edge 32. Additionally, the first panel 12 can have a second length L2 corresponding to the height or length of the angled portions 28, 30 extending along the first panel 12. Additionally, the first panel 12 has a width W1 extending between the left-side edge 24 and the right-side edge 26 corresponding to a length of the upper edge 22, and a width W3 (see FIG. 2) at the crease line 20 corresponding to a length of the lower edge 32 between the angled portion 28 of the left-side edge 24 and the angled portion 30 of the right-side edge 26. As shown in FIG. 1, the width W1 is greater than the width W3, and the difference in length between W1 and W3 can be a function of the angles θ1 and θ2.

Still referring to FIG. 1, the second panel 14, which may also be called a bottom panel, has an inner surface 54, and an opposite outer surface 56 (see FIGS. 3-5). The second panel 14 has lower edge 50 positioned at the crease line 20. The second panel 14 additionally includes an upper edge 40 that can be opposite and generally parallel to the lower edge 50, a left-side edge 42 that can extend between the upper edge 40 and the lower edge 50, and a right-side edge 44 that can extend between the upper edge 40 and the lower edge 50 opposite the left-side edge 42. The left-side edge 42 and the right-side edge 44 may each extend downward from the upper edge 40 at a perpendicular angle. Optionally, the second panel 14 may include rounded corners 52 disposed at the transition between the left-side edge 42 and the upper edge 40, and the right-side edge 44 and the upper edge 40, respectively. The left-side edge 42 can include an angled portion 46 disposed adjacent to the lower edge 50 with an angle θ3 between the angled portion 46 and the lower edge 50. The angle θ3 may be an obtuse angle greater than 90 degrees and less than 180 degrees, such as an angle in a range from about 100 degrees to about 160 degrees, such as from about 110 degrees to about 135 degrees. Additionally, the angled portion 46 may instead have a radiused or curved transition between the left-side edge 42 and/or the lower edge 50. Similarly, the right-side edge 44 can include an angled portion 48 disposed adjacent to the lower edge 50 with an angle θ4 between the angled portion 48 and the lower edge 50. The angle 84 may be an obtuse angle greater than 90 degrees and less than 180 degrees, such as an angle in a range from about 100 degrees to about 160 degrees, such as from about 110 degrees to about 135 degrees. Additionally, the angled portion 48 may instead have a radiused or curved transition between the right-side edge 44 and/or the lower edge 50. In some aspects of the invention, the angles θ3 and θ4 can be equal, and/or a radius of curvature of the angled portions 46 and 48 can be equal. Moreover, in some aspects of the invention, the second panel 12 may be bilaterally symmetrical across the midline M of the body 10 such that the left-side edge 42, the angled portion 46 of the left-side edge 42, and the angle θ3 are mirrored by the right-side edge 44, the angled portion 48 of the right-side edge 44, and the angle θ4.

As shown in FIG. 1, the second panel 14 can have a length L3 extending from the upper edge 40 to the lower edge 50. Additionally, the second panel 14 can have a length L4 corresponding to the height or length of the angled portions 46, 48 extending along the second panel 14. Additionally, the second panel 14 has a width W2 extending between the left-side edge 42 and the right-side edge 44 corresponding to a length of the upper edge 40, and a width W3 (see FIG. 2) at the crease line 20 corresponding to a length of the lower edge 50 between the angled portion 46 of the left-side edge 42 and the angled portion 48 of the right-side edge 44. As shown in FIG. 1, the width W2 is greater than the width W3, and the difference in length between W2 and W3 can be a function of the angles θ3 and θ4.

Figure 2:
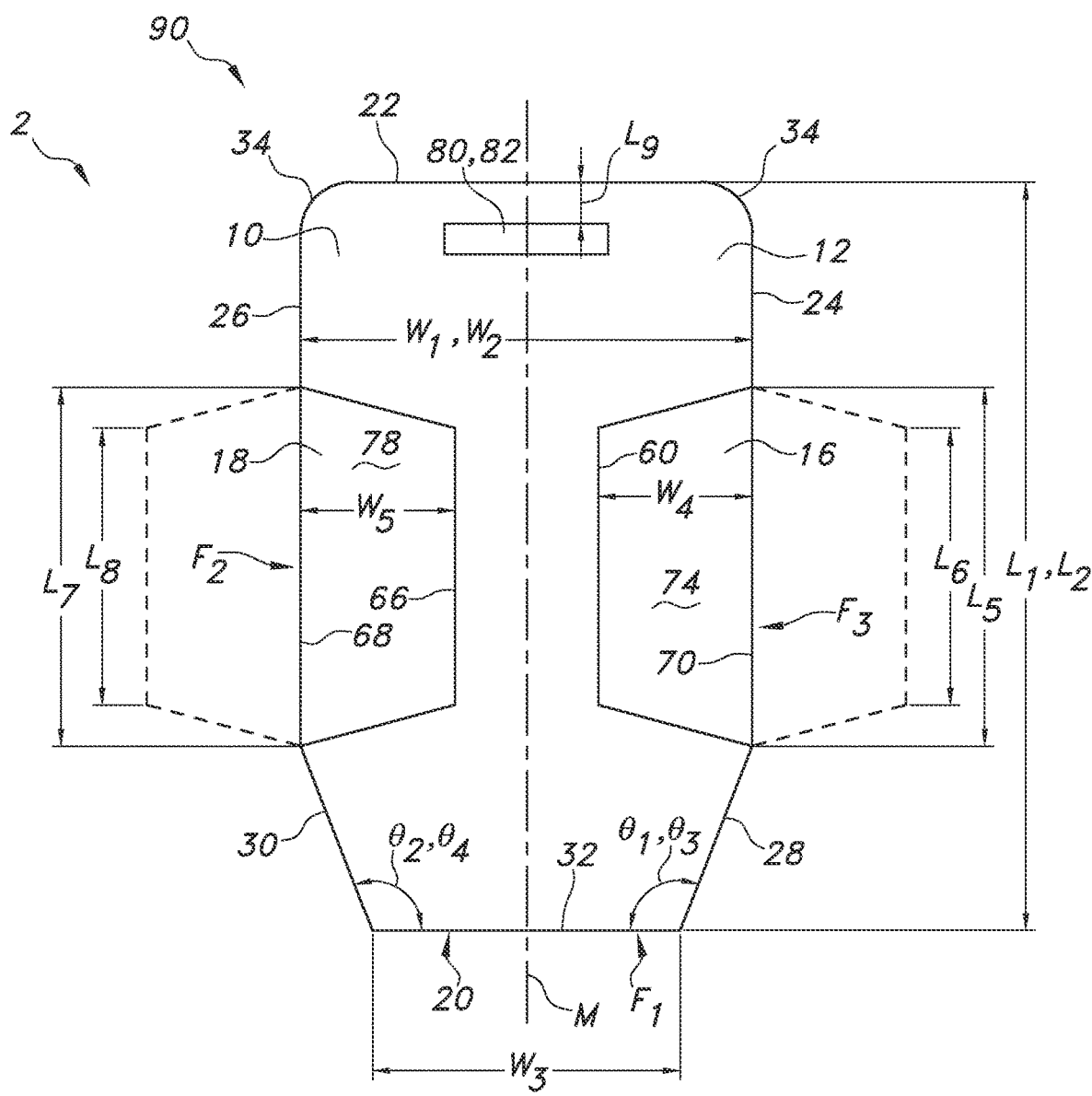
FIG. 2 illustrates a front view of the protective cover of FIG. 1 after assembly of the protective cover.

The second panel 14 as shown in FIG. 1 may include a left-side panel 16 and a right-side panel 18. The left-side panel 16 can extend from the left-side edge 42. Additionally, and corresponding to the surfaces of the second panel 14 described above, the left-side panel 16 has an inner surface 72 and an outer surface 74. The left-side panel 16 includes an outer edge 60, an inner edge 62 disposed along the left-side edge 42, and one or more side edges 64. As shown in FIG. 1, in one particular embodiment of the present invention, the left-side panel 16 can include two side edges 64 extending between the outer edge 60 and the inner edge 62. The left-side panel 16 has a length L5 along the inner edge 62, a length L6 along the outer edge 62, and a width W4 extending between the inner edge 62 and outer edge 60 (see FIG. 2). In some aspects, as shown in FIG. 1, the side edges 64 can extend from the inner edge 62 and the left-side edge 42 at an angle θ5. Both side edges 64 can extend at the same angle, or the side edges 64 can extend at different angles. The angle θ5 can be an acute angle. When the angle θ5 is an acute angle, the length L6 is shorter than the length L5, as shown in FIG. 2. However, if the angle 85 is a right angle, the lengths L5 and L6 are equal. In addition, one or more of the transitions between the side panels 64, the left-side angled portion 46 and/or the left-side edge 42 can be radiused or curved.

The right-side panel 18 can extend from the right-side edge 44. Additionally, and corresponding to the surfaces of the second panel 14 described above, the right-side panel 18 has an inner surface 76 and an outer surface 78. The right-side panel 18 includes an outer edge 66, an inner edge 68 disposed along the right-side edge 44, and one or more side edges 70. As shown in FIG. 1, in one particular embodiment of the present invention, the right-side panel 18 can include two side edges 70 extending between the outer edge 66 and the inner edge 68. The right-side panel 18 has a length L7 along the inner edge 68, a length L8 along the outer edge 66, and a width W5 extending between the inner edge 68 and outer edge 66 (see FIG. 2). In some aspects, as shown in FIG. 1, the side edges 70 can extend from the inner edge 68 and the right-side edge 44 at an angle θ6. Both side edges 70 can extend at the same angle, or the side edges 70 can extend at different angles. The angle θ6 can be an acute angle. When the angle θ6 is an acute angle, the length L8 is shorter than the length L7, as shown in FIG. 2. However, if the angle 86 is a right angle, the lengths L7 and L8 are equal. In addition, one or more of the transitions between the side panels 70, the right-side angled portion 48 and/or the right-side edge 44 can be radiused or curved.

In some aspects of the invention, as shown in FIG. 1, the left-side panel 16 and the right-side panel 18 can be symmetrical, and the angles θ5 and θ6 can be equal. Moreover, in some aspects of the invention, the entire second panel 12 may be bilaterally symmetrical across the midline M of the body 10 such that the left-side edge 42, the angled portion 46 of the left-side edge 42, the angle θ3, the left-side panel 16 and the angle θ5 are mirrored by the right-side edge 44, the angled portion 48 of the right-side edge 44, the angle θ6, the right-side panel 18 and the angle θ6. When the left-side panel 16 and the right-side panel 18 are symmetrical, the corresponding dimensions (i.e., L5 and L7; L6 and L8; W4 and W5; 85 and 86) are equal.

The first panel 12 may include an aperture 80 adjacent to the upper edge 22 and generally centrally positioned between the left-side edge 24 and the right-side edge 26. Similarly, the second panel 14 may include an aperture 82 adjacent to the upper edge 40 and generally centrally positioned between the left-side edge 42 and the right-side edge 44. The apertures 80, 82 can each be configured to receive a flange 104 of an IV spike 100. For instance, as described in further detail below, when the body 10 is formed into a protective sleeve 90 configured to receive the spike end 106 of the IV spike 100 within a protective opening 92 of the protective sleeve 90, the flange(s) 104 of the IV spike 100 can be inserted and/or held within the apertures 80, 82 to hold the IV spike 100 in place. Each of the apertures may be disposed a distance L9 from the respective upper edges 22, 40 of the first panel 12 and the second panel 14, respectively, as shown in FIG. 2, and centered on the midline M such that the apertures 80, 82 are bilaterally symmetrical across the midline M.

In some aspects of the invention, the body 10 can be formed from a single piece of material, as shown in FIG. 1. As such, the first panel 12, second panel 14, left-side panel 16 and right-side panel 18 can be formed from a single, unitary piece of material and folded to form the protective sleeve 90 of the invention. Alternatively, when desired, the body 10 can be formed from one or more pieces of material that are secured together. The body 10, and thus, the panels 12, 14, 16, 18, may be constructed of any suitable material including paper-based materials such as, for example, carton cardboard stock, paperboard, heavy structural paper, container stock, corrugated paperboard, plastic coated paper, a plastic sheet, a wax-coated paper or the like, or a combination thereof. The paper-based material(s) can be provided as a single layer or multiple layers. In some aspects of the invention, the body 10 is formed from paperboard or fiberboard, in particular, solid bleached sulfate (also known as solid bleached board). The paper-based material(s) used to form the body 10 may maintain aseptic handling and provide sufficient structural characteristics to form a secure cover for an IV spike 100 as contemplated by the present invention. Moreover, the paper-based material(s) may be biodegradable such that the protective cover 2 of the present invention is more environmentally friendly than single-use polymer-based alternatives known in the art.

Still referring to FIG. 1, the first panel 12 and the second panel 14 may be connected along the crease line 20. As shown in FIG. 1, the lower edge 32 of the first panel 12 may coincide with the lower edge 50 of the second panel 14 along the crease line 20. The crease line 20 may form a first fold line F1 along which the body 10 of the protective cover 2 is folded. For instance, the body 10 may be folded in a direction to bring the inner surface 36 of the first panel 12 near to the inner surface 54 of the second panel 14, such that the outer surface 38 of the first panel 12 and the outer surface 56 of the second panel 14 face out and away from each other.

The left-side panel 16 and the right-side panel 18 of the second panel 14 may be configured to secure the second panel 14 to the first panel 12 when the body 10 is folded along the first fold line F1. For instance, the left-side panel 16 can be folded along a second fold line F2 which extends along the inner edge 62 of the left-side panel 16/left-side edge 42 such that the outer edge 60 is brought toward the midline M and the inner surface 72 of the left-side panel 16 is brought towards the inner surface 54 of the second panel 14. Similarly, the right-side panel 18 can be folded along a third fold line F3 which extends along the inner edge 68 of the right-side panel 18/right-side edge 44 such that the outer edge 66 is brought toward the midline M and the inner surface 76 of the right-side panel 16 is brought towards the inner surface 54 of the second panel 14.

In order to secure the second panel 14 to the first panel 12, the left-side panel 16 and the right-side panel 18 can be configured to contact either the inner surface 36 or the outer surface 38 of the first panel 12. For instance, as shown in FIG. 2, the left-side panel 16 and the right-side panel 18 wrap around the first panel 12 such that the inner surfaces 72, 76 (not shown) of the left-side panel 16 and right-side panel 18, respectively, contact the outer surface 36 of the first panel 12 and the outer surfaces 74, 78 of the left-side panel 16 and the right-side panel 18, respectively, are exposed. Alternatively, as shown in FIG. 3, the outer surfaces 74, 78 of the left-side panel 16 and the right-side panel 18, respectively, can contact the inner surface 36 of the first panel 12 and the inner surfaces 72, 76 of the left-side panel 16 and the right-side panel 18, respectively, can be exposed within the protective opening 92 of the protective sleeve 90 that is formed when the first panel 12 and second panel 14 are secured together. The left-side panel 16 and right-side panel 18 of the second panel 14 can be secured to the first panel 12 by any suitable means, such as adhesives 94 such as glue. The securement can be a permanent attachment or a reversible attachment that can facilitate detachment of the side panels 16, 18 from the first panel 12. In one aspect of the invention, the side panels 16, 18 can be glued to the first panel 12.

Still referring to FIG. 2, when the body 10 is folded along the first fold line F1 such that the inner surfaces 36, 54 of the first panel 12 and the second panel 14, respectively, are brought near to each other, and the left-side panel 16 and the right-side panel 18 are folded toward the second panel 14 along the second fold line F2 and third fold line F3, respectively, the first panel 12 and the second panel 14 may be symmetrical across the crease 20 or fold line F1. When the first panel 12 and the second panel 14 are symmetrical, each of the corresponding dimensions of the first panel 12 and the second panel 14 (i.e., L1 and L2; W1 and W2) are equal. Further, the angles θ1 and θ3 can be equal, and the angles θ2 and θ4 can be equal. In some aspects of the invention, all of the angles θ1, θ2, θ3 and θ4 may be equal, as shown in FIG. 2. Moreover, when the body 10 is folded to form the protective sleeve 90 as shown in FIG. 2, the apertures 80 and 82 may align with each other.

As best seen in FIGS. 3 and 5, when the body 10 is formed into the protective sleeve 90, a protective opening 92 is formed between the first panel 12 and the second panel 14 such that a spike end 106 of an IV spike can be inserted in the protective opening 92 toward the crease line 20. The body 102 of the IV spike opposite the spike end 106 may extend from the protective opening 92, as shown in FIGS. 4 and 5. One or more flanges 104 of the IV spike can extend through the apertures 80, 82 of the first panel 12 and the second panel 14, respectively, to hold the IV spike 100 in place within the protective sleeve 90.

In some aspects of the invention, the protective sleeve 90 may be sized and dimensioned to snugly fit the IV spike body 102. A snug fit between the IV spike body 102 and the protective sleeve 90 can help to maintain aseptic handling of the spike end 106 of the IV spike.

The protective cover 2 of the present invention is configured to provide a package and/or protection during storage and transport for any medical spike product such as the IV spike 100 shown in FIG. 7. The IV spike includes a body 102 having a spike end 106 and one or more flanges 104 extending from the body 102. However, it is to be understood that the protective cover 2 of the present invention can be adapted to form a protective sleeve 90 for any suitable medical spike product. For instance, the dimensions (i.e., lengths, widths, and/or angles) of the protective cover 2 can be modified to provide a custom fit for any medical spike product.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A medical spike product assembly comprising:
   a medical spike product comprising a body having a spike end; and
   a protective cover for the medical spike product having:
   a first panel having a lower edge and first and second side edges; and
   a second panel having a lower edge and first and second side edges,
   wherein the first panel and the second panel are connected at their lower edges and first and second side edges, respectively;
   wherein the first panel and the second panel are configured to be spaced apart to form a protective sleeve;
   wherein the first panel and the second panel each comprise an aperture adjacent to an upper edge of the first panel and the second panel, respectively, and wherein the aperture is configured to receive a portion of the medical spike product to hold the spike end of the medical spike product within the protective sleeve;
   wherein the spike end of the medical spike product is inserted within the protective sleeve such that the first panel and the second panel protectively cover the spike end of the medical spike product.

2. The medical spike product assembly of claim 1, wherein the body of the medical spike product comprises opposing wings extending perpendicular to the spike end, further wherein the first panel and the second panel of the protective cover each comprises an aperture configured to receive the respective opposing wings of the medical spike product in order to hold the spike end of the medical spike product within the protective sleeve;
   wherein the opposing wings of the medical spike product are configured to be disengaged from the apertures of the first panel and the second panel, respectively, by squeezing the first and second side edges of the first panel and the second panel to separate the first panel from the second panel.

3. The medical spike product assembly of claim 1, wherein the body of the medical spike product comprises opposing wings extending perpendicular to the spike end, further wherein the first panel and the second panel of the protective cover each comprises an aperture configured to receive the respective opposing wings of the medical spike product in order to hold the spike end of the medical spike product within the protective sleeve;
   wherein the opposing wings of the medical spike product are configured to be forcibly removed from the apertures of the first panel and the second panel, respectively, by tearing an upper edge of each respective aperture.

4. The medical spike product assembly of claim 1, wherein the first panel of the protective cover comprises an upper edge opposite the lower edge of the first panel, a right-side edge, and a left-side edge, wherein the right-side edge comprises a right-side angled portion adjacent to the lower edge, and the left-side edge comprises a left-side angled portion adjacent to the lower edge.

5. The medical spike product assembly of claim 4, wherein a first right-side angle is formed between the right-side angled portion and the lower edge, and a first left-side angle is formed between the left-side angled portion and the lower edge.

6. The medical spike product assembly of claim 5, wherein the first right-side angle and the first left-side angle are obtuse.

7. The medical spike product assembly of claim 5, wherein the first right-side angle and the first left-side angle are equal.

8. The medical spike product assembly of claim 1, wherein the second panel of the protective cover comprises an upper edge opposite the lower edge of the second panel, a right-side edge, and a left-side edge, wherein the right-side edge comprises a right-side angled portion adjacent to the lower edge, and the left-side edge comprises a left-side angled portion adjacent to the lower edge.

9. The medical spike product assembly of claim 8, wherein a second right-side angle is formed between the right-side angled portion of the second panel and the lower edge of the second panel, and a second left-side angle is formed between the left-side angled portion of the second panel and the lower edge of the second panel.

10. The medical spike product assembly of claim 9, wherein a first right-side angle is formed between the right-side angled portion and the lower edge,
    wherein the second right-side angle is equal to the first right-side angle, and the second left-side angle is equal to the first right-side angle.

11. The medical spike product assembly of claim 1, wherein the first panel and the second panel are bilaterally symmetrical.

12. The medical spike product assembly of claim 1, wherein the second panel of the protective cover comprises: a right-side edge, a right-side panel extending from the right-side edge, a left-side edge and a left-side panel extending from the left-side edge;

wherein the right-side panel and the left-side panel are configured to be secured to the first panel to form a protective opening between the first panel and the second panel.

13. The medical spike product assembly of claim 12, wherein the second panel of the protective cover comprises a right-side fold line between the right-side edge and the right-side panel, and a left-side fold line between the left-side edge and the left-side panel;

wherein the right-side panel is folded toward the second panel along the right-side fold line and the left-side panel is folded toward the second panel along the left-side fold line.

14. The medical spike product assembly of claim 13, wherein the right-side panel is secured to the first panel and the left-side panel is secured to the first panel.

15. The medical spike product assembly of claim 14, wherein the right-side panel and the left-side panel are secured to the first panel with adhesive.

16. The medical spike product assembly of claim 1, wherein the protective cover is formed from a single piece of material.

17. The medical spike product assembly of claim 16, wherein the single piece of material comprises a crease line along a bottom edge of the first panel and a bottom edge of the second panel;

wherein the single piece of material is folded along the crease line to bring an inner surface of the first panel adjacent to an inner surface of the second panel.

18. The medical spike product assembly of claim 1, wherein the protective cover is formed from a paper-based material.

19. The medical spike product assembly of claim 18, wherein the paper-based material is solid bleached sulfate.

20. The medical spike product assembly of claim 1, wherein the protective cover is formed from a biodegradable material.

\* \* \* \* \*